(12) United States Patent
Freeman et al.

(10) Patent No.: US 10,772,358 B2
(45) Date of Patent: Sep. 15, 2020

(54) INHALATION DEVICE HAVING SECURITY FEATURES

(71) Applicant: INDOSE INC, Woodland Hills, CA (US)

(72) Inventors: Daniel Freeman, Agoura, CA (US); Ari Freeman, Lafayette, CA (US); Jacqueline Freeman, Lafayette, CA (US)

(73) Assignee: INDOSE INC, Woodland Hills, CA (US)

( * ) Notice: Subject to any disclaimer, the term of this patent is extended or adjusted under 35 U.S.C. 154(b) by 0 days.

(21) Appl. No.: 15/979,591

(22) Filed: May 15, 2018

(65) Prior Publication Data

US 2018/0295886 A1 Oct. 18, 2018
US 2019/0230984 A9 Aug. 1, 2019

Related U.S. Application Data

(63) Continuation-in-part of application No. 15/244,518, filed on Aug. 23, 2016, now Pat. No. 10,599,562.
(Continued)

(51) Int. Cl.
*A24F 40/49* (2020.01)
*A24F 47/00* (2020.01)
(Continued)

(52) U.S. Cl.
CPC .......... *A24F 47/008* (2013.01); *A24F 40/49* (2020.01); *A61M 15/0065* (2013.01);
(Continued)

(58) Field of Classification Search
None
See application file for complete search history.

(56) References Cited

U.S. PATENT DOCUMENTS 5,881,715 A 3/1999 Shibasaki
9,072,321 B2 7/2015 Liu
(Continued)

FOREIGN PATENT DOCUMENTS

DK 2430252 3/2007
GB 2524779 A 10/2015
(Continued)

OTHER PUBLICATIONS

Communication from the Australian Patent Office dated Jul. 4, 2019, in Application No. 2017316131 (3 pages total).
(Continued)

*Primary Examiner* — Michael J Felton
*Assistant Examiner* — Katherine A Will
(74) *Attorney, Agent, or Firm* — Sughrue Mion, PLLC; Richard C. Turner

(57) ABSTRACT

An inhalation device for inhaling a vaporized substance that provides security and/or childproof capability that includes an inlet, an outlet, a channel positioned between the inlet and outlet, a security mechanism capable of configuring the inhalation device in a locked mode and an unlocked mode, where the inhalation device is configured to vaporize an unvaporized substance when the security mechanism configures the inhalation device in the unlocked mode, where the security mechanism is configured to prevent the inhalation device from vaporizing an unvaporized substance when the security mechanism configures the inhalation device in the locked mode.

9 Claims, 4 Drawing Sheets

Related U.S. Application Data

(60) Provisional application No. 62/621,795, filed on Jan. 25, 2018, provisional application No. 62/388,066, filed on Jan. 13, 2016, provisional application No. 62/386,614, filed on Dec. 7, 2015, provisional application No. 62/386,615, filed on Dec. 7, 2015.

(51) Int. Cl.
| | | |
|---|---|---|
| *A61M 15/00* | (2006.01) | |
| *F22B 1/28* | (2006.01) | |
| *A61M 15/06* | (2006.01) | |
| *A61M 16/00* | (2006.01) | |
| *A61M 11/04* | (2006.01) | |

(52) U.S. Cl.
CPC ........ *A61M 15/0086* (2013.01); *A61M 15/06* (2013.01); *F22B 1/284* (2013.01); *A61M 11/042* (2014.02); *A61M 15/0001* (2014.02); *A61M 2016/0021* (2013.01); *A61M 2016/0027* (2013.01); *A61M 2016/0039* (2013.01); *A61M 2205/3653* (2013.01)

(56) References Cited

U.S. PATENT DOCUMENTS

| | | | |
|---|---|---|---|
| 9,913,493 B2* | 3/2018 | Worm | A24F 47/008 |
| 2004/0089314 A1 | 5/2004 | Felter et al. | |
| 2005/0016550 A1 | 1/2005 | Katase | |
| 2005/0068528 A1 | 3/2005 | Altobelli et al. | |
| 2005/0072421 A1 | 4/2005 | Suman | |
| 2005/0247312 A1 | 11/2005 | Davies | |
| 2008/0017197 A1 | 1/2008 | Kaneko | |
| 2010/0307518 A1 | 12/2010 | Wang | |
| 2010/0313901 A1 | 12/2010 | Fernando et al. | |
| 2011/0265806 A1 | 11/2011 | Alarcon et al. | |
| 2013/0192595 A1 | 8/2013 | Tolmie et al. | |
| 2013/0276799 A1 | 10/2013 | Davidson et al. | |
| 2014/0069424 A1 | 3/2014 | Poston | |
| 2015/0122252 A1* | 5/2015 | Frija | A24F 47/008 128/202.21 |
| 2015/0181945 A1 | 7/2015 | Tremblay | |
| 2015/0216237 A1 | 8/2015 | Wensley et al. | |
| 2015/0257447 A1* | 9/2015 | Sullivan | A24F 47/008 131/329 |
| 2016/0050975 A1 | 2/2016 | Worm et al. | |
| 2016/0286865 A1* | 10/2016 | King | A24F 47/008 |
| 2016/0367925 A1* | 12/2016 | Blackley | A24F 47/008 |
| 2017/0027224 A1* | 2/2017 | Volodarsky | H05B 1/0227 |
| 2017/0086496 A1 | 3/2017 | Cameron | |
| 2017/0099877 A1* | 4/2017 | Worm | A61M 11/042 |
| 2017/0245550 A1* | 8/2017 | Freelander | A61M 15/06 |
| 2018/0110939 A1 | 4/2018 | Lanzkowsky | |
| 2019/0166913 A1* | 6/2019 | Trzecieski | A61M 11/042 |

FOREIGN PATENT DOCUMENTS

| | | |
|---|---|---|
| WO | 2011033396 A2 | 3/2011 |
| WO | 2015/179002 A2 | 11/2015 |
| WO | 2016/039625 A1 | 3/2016 |
| WO | 2016/101203 A1 | 6/2016 |
| WO | 2016/198266 A1 | 12/2016 |
| WO | 2017/001817 A1 | 1/2017 |

OTHER PUBLICATIONS

International Search Report in International Application No. PCT/US2017/019033, dated Nov. 27, 2017 (4 pages total).

Written Opinion in International Application No. PCT/US2017/019033, dated Nov. 27, 2017 (6 pages total).

Written Opinion in International Application No. PCT/US2019/031281, dated Jul. 24, 2019 (6 pages total).

International Search Report in International Application No. PCT/US2019/031281, dated Jul. 24, 2019 (6 pages total).

* cited by examiner

INHALATION DEVICE HAVING SECURITY FEATURES

This application is a continuation-in-part of and claims priority to U.S. patent application Ser. No. 15/244,518, filed on Aug. 23, 2016, which in turn claims priority to U.S. Provisional Patent Application Nos. 62/386,614 and 62/386,615, both of which were filed on Dec. 7, 2015, and 62/388,066, which was filed on Jan. 13, 2016. This application also claim priority to U.S. Provisional Patent Application No. 62/621,795 filed on Jan. 25, 2018. All of these applications are incorporated by reference herein in their entireties.

BACKGROUND

Inhaling devices such as vaporizers, vaporizing pens, and vaporizing machines are used to vaporize substances such as tobaccos, oils, liquids, medical drugs, and plant herbs. Once vaporized, these substances are then inhaled by consumers. Such inhaling devices have health benefits over traditional smoking methods. But inhaling the vapor can have negative effects on the body depending on the substance, such as nicotine. Inhaling devices have become more popular with consumers, but pose problems.

For example, while vaporizers can be safer than traditional smoking methods, it is difficult to meter the amount of vaporized substance that is being inhaled. These devices, however, can present issues. For example, they pose a risk to children. Vaporizers can be portable and battery operated and many of them can be easily turned on and used. In fact, some do not have any on/off button and are instantly turned on by inhaling from them. Unintended users may inhale the vapor without intending or knowing. Inhaling from a vaporizer can be extremely dangerous for a child if the vapor contains harmful substances. Moreover, ingesting such a vapor can go undetected by the child since some vaporizers do not have the harsh taste and coughing effect of a cigarette.

Another issue is that vaporizes are typically meant for personal use. Many times vaporizers contain product that is meant to be used by a specific person and not to be shared or used by others. Vaporizers do not include mechanisms to ensure that they are used by authorized persons.

Another issue is that vaporizers can be accidentally turned on, given the ease with which they can be used. And because parts within a vaporizer can get extremely hot (approximately 400 degrees), accidentally turning on a vaporizer can have dangerous consequences.

SUMMARY

Various aspects and embodiments of inhalation devices are provided in this disclosure. In one embodiment, this disclosure provides security and/or childproof capability that includes an inlet, an outlet, a channel positioned between the inlet and outlet, a security mechanism capable of configuring the inhalation device in a locked mode and an unlocked mode, where the inhalation device is configured to vaporize an unvaporized substance when the security mechanism configures the inhalation device in the unlocked mode, where the security mechanism is configured to prevent the inhalation device from vaporizing an unvaporized substance when the security mechanism configures the inhalation device in the locked mode.

In another aspect, the disclosure provides an inhalation device inhalation device for inhaling a vaporized substance including an inlet; an outlet; a channel positioned between the inlet and outlet; a security mechanism having a lock configured to be in a locked position or an unlocked position; where the inhalation device is configured to vaporize an unvaporized substance when the lock is in a locked position; where the security mechanism is configured to prevent the inhalation device from vaporizing an unvaporized substance when the lock is in an unlocked position.

In yet another embodiment, this disclosure provides, an inhalation device for inhaling a vaporized substance comprising: an inlet; an outlet; a channel positioned between the inlet and outlet; a security mechanism comprising a biometric sensor capable of configuring the inhalation device in a locked mode and an unlocked mode; where the inhalation device is configured to vaporize an unvaporized substance when the security mechanism configures the inhalation device in the unlocked mode; where the security mechanism is configured to prevent the inhalation device from vaporizing an unvaporized substance when the security mechanism configures the inhalation device in the locked mode.

DETAILED DESCRIPTION

As described in various embodiments herein, this disclosure provides an inhalation device with one or more security features that prevent unauthorized use of the inhalation device. The security features described in the embodiments herein prevent, for example, children who may have access to the inhalation device, from activating it. More broadly, the embodiments herein describe various ways in which unauthorized use of the inhalation device can be prevented. Generally, the inhalation device with one or more security features can have a lock/unlock and/or an activate/deactivate feature. The security device can be a mechanical, electrical, and/or a software. When the inhalation device is locked or deactivated, the device will not produce vapor or smoke. In other words, the device will not function as an inhalation device.

Figure 1:
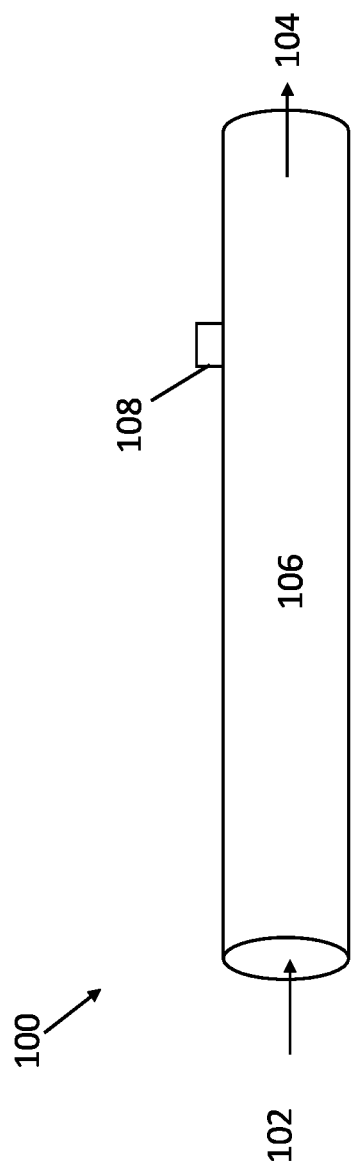
FIG. 1 is a diagram of an inhalation device.

FIG. 1 illustrates an inhalation device 100 for inhaling a vaporized substance. The inhalation device 100 includes a first opening 102 and a second opening 104. In between the two openings is a channel 106. When a user inhales using the inhalation device 100, air flows into the first opening 102 and in the device 100, vaporized substance is created by a heating element such as an atomizer (not shown), and a mixture of air and vapor flows through the channel 106 to the second opening 104 and ultimately to the user. It should be understood that this description of the inhalation device is provided for illustration only. Those with ordinary skill in the art will recognize that the security features described herein can be applied to other known inhalation devices without departing from the scope of this disclosure.

Continuing with FIG. 1, the security device includes a button 108 that is pressed in a pre-programmed or customized pattern which would unlock the vaporizing ability. This can be implemented for example, with a processor that compares the user's inputted pattern with a pre-determined pattern that can be stored on the inhalation device such as on the processor, or stored remotely, or any other suitable place where the pattern can be stored. This pattern, for example, could be a Morse code sequence that could act as a passcode to enable the device. The code could comprise presses of various lengths and pauses of various lengths. Use of a button in this manner would allow for complex codes with a single button.

Figure 2:
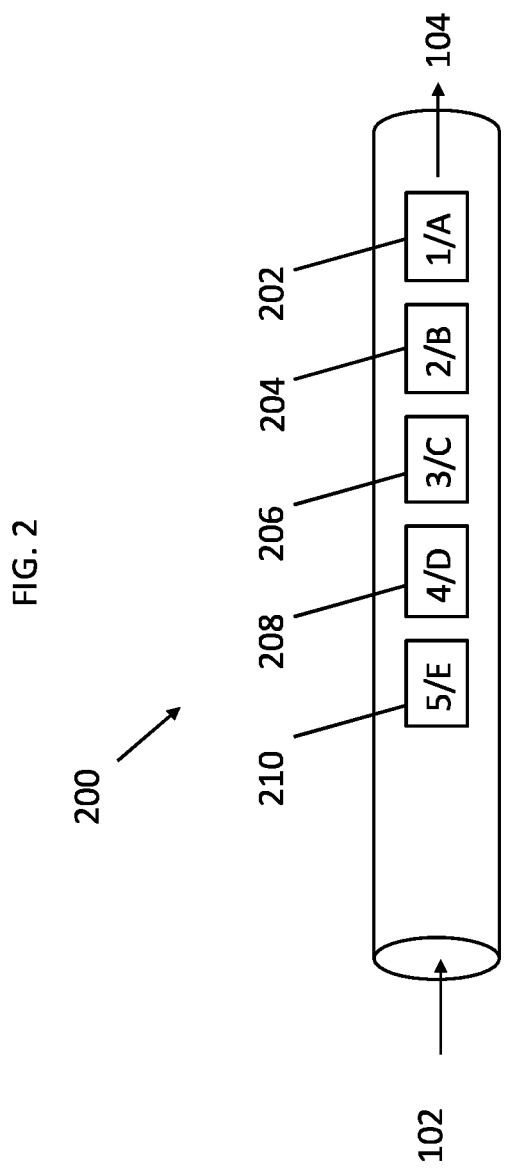
FIG. 2 is another diagram of an inhalation device, according to an embodiment of this disclosure.

FIG. 2 illustrates another inhalation device 200 according to another embodiment of this disclosure. Inhalation device 200 includes a security mechanism that comprises a plurality of buttons 202, 204, 206, 208, and 210. The buttons 202-210 are shown with identifiers 1-5 and A-E. The buttons 202-210 allow for a user to input a passcode as a combination of letter and/or numbers in order to unlock the inhalation device. It should be understood that the buttons could include only numbers, only letters, and mix of both, or have no identifiers. Users can use the buttons 202-210 to enter a passcode made up of a sequence of button presses.

Figure 3:
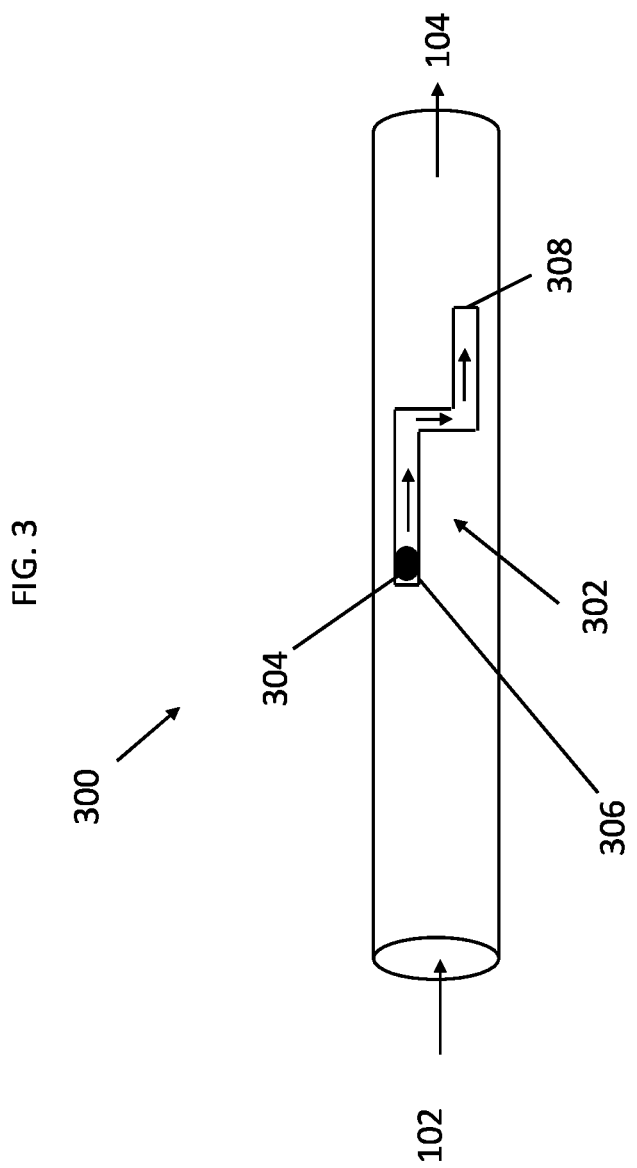
FIG. 3 is another diagram of an inhalation device, according to an embodiment of this disclosure.

While embodiments shown in FIGS. 1 and 2 involve pressing one or more buttons, other security mechanisms could be used without departing from the scope of this disclosure. For example, FIG. 3 illustrates an inhalation device 300 having a mechanical locking device 302 having a slide 304. The inhalation device 300 can be activated when the user slides the slide 804 as indicated by the arrows. In the embodiment of FIG. 3, the locking device 302 is at a first end 306 of the slide 304 at a position that locks the inhalation device. When a user moves the locking device 302 along arrows as indicated to the second end 308 of the slide 304, the locking device 302 is at a position that unlocks the locking device. While the slide 304 is illustrating as having three rectangular portions is should be understood that other shapes for the slides, such as fewer than three rectangles, curved portions, S-shapes, can be used without departing from the scope of this disclosure. In addition, the slide can be implemented to include resistance making it difficult for a child's dexterity to enable. Alternatively, an inhalation device with a mechanical locking device could be activated with the user's hand, teeth, tongue, blowing, sucking and/or by shaking. For example, a passcode can be entered by inhaling or exhaling on the vaporizer. The inhales and or exhales would act in place of button presses and allow the user to enter a Morse code style passcode. This can be implemented using a sensor, such as a pressure sensor, and air flow sensor to allow the consumer to communicate with the device using a passcode. Other suitable sensors that could be implemented to communicate a passcode to the device could be touch or heat sensors.

Figure 4:
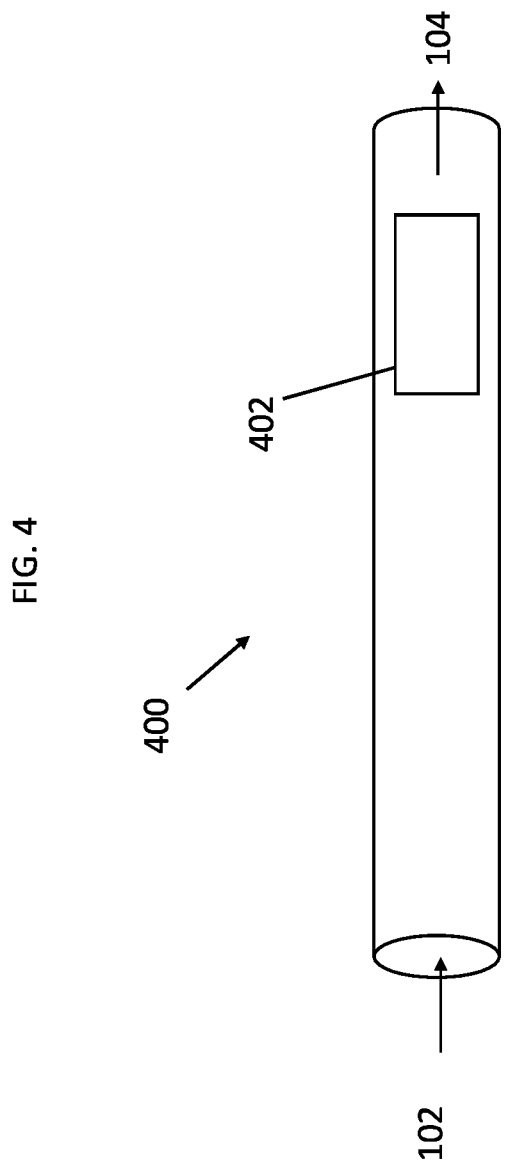
FIG. 4 is another diagram of an inhalation device, according to an embodiment of this disclosure.

Other options include a software key, passcode or biometric reading to enable the device. As to software, embodiments of a security device could include software that allows users to create multiple passcodes which would have multiple restrictions or parameters such as: user identification information, limit usage, limit drug dosage, and auto lock settings. FIG. 4 illustrates an inhalation device 400, with a security device 402. The security device 402 can be a biometric sensor wherein the biometric sensor can be programmed to recognize specific users, such as for example a finger print. The biometric sensor alternatively could include detecting a particular swipe pattern with the user's finger on the device. In another embodiment of the security device, the security device 402 could include a touch screen where the user would be able to enter into the touchscreen a passcode to unlock or activate the vaporizer. Alternatively, a finger print reader could be implemented.

While embodiments have been illustrated and described herein, it is appreciated that various substitutions and changes in the described embodiments may be made by those skilled in the art without departing from the spirit of this disclosure. The embodiments described herein are for illustration and not intended to limit the scope of this disclosure.

The invention claimed is:

1. An inhalation device for inhaling a vaporized substance, the inhalation device comprising:
   a housing;
   an inlet;
   an outlet,
   a channel positioned between the inlet and the outlet inside the housing; and
   a security mechanism capable of configuring the inhalation device in a locked mode and an unlocked mode,
   wherein, the inhalation device is configured to vaporize an unvaporized substance when the security mechanism configures the inhalation device in the unlocked mode,
   the security mechanism is configured to prevent the inhalation device from vaporizing the unvaporized substance when the security mechanism configures the inhalation device in the locked mode,
   the security mechanism comprises at least one button installed in a surface of the housing,
   the security mechanism is further configured to, based on a user applying pressure to the at least one button in a predetermined manner, control, the inhalation device to become unlocked to enable vaporization of the unvaporized substance,
   the predetermined manner is a timed pattern, and
   the timed pattern comprises a Morse code pattern.

2. An inhalation device for inhaling a vaporized substance, the inhalation device comprising:
   a housing;
   an inlet;
   an outlet;
   a channel positioned between the inlet and the outlet inside the housing; and
   a security mechanism having a lock configured to be in a locked position or an unlocked position,
   wherein the inhalation device is configured to vaporize an unvaporized substance when the lock is in the unlocked position,
   wherein the security mechanism is configured to prevent the inhalation device from vaporizing the unvaporized substance when the lock is in the locked position,
   wherein the security mechanism includes a slide formed in a surface of the housing as at least two members disposed at an angle with respect to each other,
   wherein, the lock is configured to move from the locked position to the unlocked position via the slide, and
   wherein the lock is configured to move from the locked position to the unlocked position by a user inhaling or exhaling in a predetermined pattern.

3. The inhalation device of claim 2, wherein the slide further includes at least one curved portion.

4. The inhalation device of claim 2, wherein the lock is configured to have resistance making it difficult for a child to move the lock from the locked position to the unlocked position.

5. The inhalation device of claim 2, further comprising a sensor configured to detect the predetermined pattern based on the user inhaling or exhaling.

6. An inhalation device for inhaling a vaporized substance, the inhalation device comprising:
   an inlet;
   an outlet;

a channel positioned between the inlet and the outlet; and a security mechanism having a lock configured to be in a locked position or an unlocked position, wherein, the inhalation device is configured to vaporize an unvaporized substance when the lock is in the unlocked position, wherein the security mechanism, is configured to prevent the inhalation device from vaporizing the unvaporized substance when the lock is in the locked position, and wherein the lock is configured to move from the locked position to the unlocked position based on a user performing at least one of inhaling or exhaling in one from among a sequence and a pattern that is predetermined as a passcode for the user.

7. The inhalation device of claim 6, wherein the lock is configured to move from the locked position to the unlocked position based on the security mechanism identifying the passcode based on, a timed pattern.

8. The inhalation, device of claim 7, wherein the timed pattern comprises a Morse code pattern.

9. The inhalation device of claim 6, further comprising:

one from among a pressure sensor and an air flow sensor that are configured to detect the passcode.

\* \* \* \* \*